(12) United States Patent
Kwiatkowski et al.

(10) Patent No.: US 7,315,758 B2
(45) Date of Patent: Jan. 1, 2008

(54) TRANSDERMAL DELIVERY OF THERAPEUTIC AGENT

(75) Inventors: Krzysztof C. Kwiatkowski, College Station, TX (US); Ryan T. Hayes, College Station, TX (US); James W. Magnuson, College Station, TX (US); Anthony Giletto, College Station, TX (US)

(73) Assignee: Lynntech, Inc., College Station, TX (US)

( * ) Notice: Subject to any disclaimer, the term of this patent is extended or adjusted under 35 U.S.C. 154(b) by 769 days.

(21) Appl. No.: 10/860,557

(22) Filed: Jun. 3, 2004

(65) Prior Publication Data

US 2005/0273046 A1 Dec. 8, 2005

(51) Int. Cl.
*A61N 1/30* (2006.01)
(52) U.S. Cl. .......................................... 604/21; 604/501
(58) Field of Classification Search ................. 604/20, 604/21, 500, 501
See application file for complete search history.

(56) References Cited

U.S. PATENT DOCUMENTS

| | | | |
|---|---|---|---|
| 3,964,482 A | 6/1976 | Gerstel et al. | |
| 5,533,972 A | 7/1996 | Gyory et al. | |
| 5,547,467 A * | 8/1996 | Pliquett et al. | 604/20 |
| 5,667,491 A * | 9/1997 | Pliquett et al. | 604/501 |
| 5,879,326 A | 3/1999 | Godshall et al. | |
| 5,911,223 A * | 6/1999 | Weaver et al. | 128/898 |
| 6,302,874 B1 * | 10/2001 | Zhang et al. | 604/522 |
| 6,312,612 B1 | 11/2001 | Sherman et al. | |
| 6,314,317 B1 | 11/2001 | Willis | |
| 6,379,324 B1 | 4/2002 | Gartstein et al. | |
| 6,512,950 B2 | 1/2003 | Li et al. | |
| 6,532,386 B2 | 3/2003 | Sun et al. | |
| 6,553,253 B1 | 4/2003 | Chang | |
| 6,582,416 B2 | 6/2003 | Tapper | |
| 6,589,202 B1 | 7/2003 | Powell | |
| 6,616,949 B2 | 9/2003 | Jönsson et al. | |
| 6,678,556 B1 * | 1/2004 | Nolan et al. | 604/21 |
| 6,706,016 B2 * | 3/2004 | Cory et al. | 604/117 |
| 6,972,013 B1 * | 12/2005 | Zhang et al. | 604/501 |

FOREIGN PATENT DOCUMENTS

| | | |
|---|---|---|
| WO | WO 97/48440 | 6/1997 |
| WO | WO 98/00193 | 7/1997 |

* cited by examiner

*Primary Examiner*—Sharon Kennedy
(74) *Attorney, Agent, or Firm*—Jeffrey L. Streets; Streets & Steele (57) ABSTRACT

A device for the transdermal delivery of a therapeutic agent to a biological subject that includes a first electrode comprising a first array of electrically conductive microprojections for providing electrical communication through a skin portion of the subject to a second electrode comprising a second array of electrically conductive microprojections. Additionally, a reservoir for holding the therapeutic agent surrounding the first electrode and a pulse generator for providing an exponential decay pulse between the first and second electrodes may be provided. A method includes the steps of piercing a stratum corneum layer of skin with two arrays of conductive microprojections, encapsulating the therapeutic agent into biocompatible charged carriers, surrounding the conductive microprojections with the therapeutic agent, generating an exponential decay pulse between the two arrays of conductive microprojections to create a non-uniform electrical field and electrokinetically driving the therapeutic agent through the stratum corneum layer of skin.

49 Claims, 4 Drawing Sheets

TRANSDERMAL DELIVERY OF THERAPEUTIC AGENT

This invention was made with government support under contract number NAS3-03033 awarded by the National Aeronautics and Space Administration (NASA). The government has certain rights in this invention.

BACKGROUND OF THE INVENTION

1. Field of the Invention

The present invention relates to medical devices, and more specifically, to an apparatus and method for transdermal delivery of pharmaceuticals.

2. Description of the Related Art

Common methods for administering therapeutic molecules to treat illnesses or injuries to a patient include the use of hypodermic needles and oral ingestion. These methods have limitations. Delivery by oral ingestion or injection by hypodermic syringe can cause drug concentrations in the body to fluctuate between high and low values, whereas a sustained or continuous delivery is desirable. Hypodermic needle delivery is very unpopular with patients, who are often reluctant to perform this procedure on themselves. Furthermore, safe handling and disposal of the biohazardous hypodermic needles is difficult.

Oral administration of drugs remains the most common method of drug delivery because the cells lining the intestine tend to be quite permeable and because oral ingestion is generally accepted by patients. This approach, however, has a variety of shortcomings including degradation of the agent within the digestive system, local gastrointestinal irritation, and noncompliance when patients do not take their prescription in a timely manner. Furthermore, some of the drugs resulting from advances in biotechnology are protein based and cannot be taken orally or they will be digested in the gastrointestinal tract. These difficulties have spurred research into new ways to deliver therapeutic molecules, preferably by non-invasive or semi-invasive paths. Examples include jet injectors, inhalers, and external micropumps. Unfortunately, there are problems associated with the few commercially available non-invasive or semi-invasive delivery devices.

One non-invasive method of administering drugs being widely studied is the transcutaneous delivery method. The transport of various agents such as metabolites, drugs and nutrients across tissues is a function primarily of three factors: tissue permeability, the presence or absence of a driving force and the size of the area through which transport occurs. The lack of inherent permeability for many tissues renders it difficult to move agents across a body surface. The permeability of many tissues is low because cell membranes are generally composed of lipid bilayers that are relatively impermeable to ionized and uncharged polar species. For example, transport of agents across the skin has proven difficult in part because the outer layer of skin, termed the stratum corneum, consists of tightly packed cells with intercellular lipids that severely impede the passage of substances through this barrier.

Medicated adhesive patches provide one method for the transcutaneous administration of drugs. The drug is pre-loaded and steadily diffuses from the patch through the skin to blood capillaries in the skin's deeper layers. Drug patches are popular for several reasons: 1) they allow sustained drug delivery, avoiding the concentration peaks and valleys of conventional methods, 2) patients are less likely to forget, 3) the drugs are delivered painlessly, and 4) degradation of the drug by the GI tract is not an issue. Today transdermal patches delivery estrogen for hormone replacement therapy, nitroglycerine for angina, scopolamine for motion sickness and seasickness, fentanyl for pain control, clonidine for hypertension, and recently ethinylestradiol plus norelgestromin for contraception.

Despite these advantages, wearable patches are constrained by the fact that very few drugs can be formulated for transdermal delivery. The limitation comes from the highly resistive outer-most layer of the skin, the stratum corneum. Drugs delivered transdermally must be small enough to diffuse through the lipophillic gaps between the skin cells and through the skin pores. For this passive delivery, drugs must have a large therapeutic window; they must not be toxic at high concentrations yet still potent at low concentrations. Unfortunately, very few drugs meet this requirement. The benefits of wearable patches will not be realized unless methods to enhance drug passage through the stratum corneum are developed.

Iontophoresis is an alternative approach that can be utilized to deliver agents across a tissue by the application of an electrical current. In practice, iontophoretic methods generally provide positioning an electrode having a reservoir or absorbent pad that contains the agent to be transferred onto the tissue through which delivery is to occur. Another electrode that typically does not include the agent but contains, or is coated with, a conductive gel is also placed in contact with the tissue to complete the electrical circuit.

Application of a voltage between the two electrodes and across the tissue generates a current that causes the ionized agent to move towards the electrode of opposite charge, thereby driving the agent through the tissue. Neutral agents can also be transported, albeit less effectively than ionized agents, via electroosmosis. Iontophoresis also may induce the formation and/or enlargement of pores within tissues, which in turn increases tissue permeability to ionic and polar agents and drives these agents through the enlarged pores. When the tissue is skin, the agent penetrates the stratum corneum and then passes through the other layers of the epidermis into the dermis layer, the second major layer of skin. The innermost portion of the dermis is typically referred to as the papillary layer and contains a network of capillaries from the vascular system. This network absorbs the therapeutic agent and subsequently moves it to the main portion of the circulatory system. A problem associated with drug administration using iontophoresis is that it is applicable only to drugs that have an electrical charge.

While iontophoresis typically utilizes a DC power source to provide a DC current, AC current may also be used for iontophoresis. For example, U.S. Pat. No. 6,512,950 issued to Li, et al., and hereby fully incorporated by reference, discloses a variety of methods for transporting agents across tissue. The disclosed methods utilize an AC signal to maintain a substantially constant electrical state in a region of the tissue through which transport occurs, thereby allowing the agent to be transported across the issue in a controlled and predictable manner.

Another method found to be useful for increasing the transdermal passage of therapeutic agents has been to perforate the stratum corneum with microprojections. Perforating the stratum corneum with an array of microprojections that have very sharp tips, typically having a diameter of between about 1μ and about 2 μm, significantly reduces the current required for iontophoresis. U.S. Pat. No. 6,379,324 issued to Gartstein and herein incorporated by reference in its entirety, discloses a microneedle array constructed of silicon and silicon dioxide compounds that may be used to perforate the stratum corneum of the skin to deliver drugs into the epidermis through the application of iontophoresis.

There is a need to provide caregivers and their patients with procedures and devices that may be used to administer metabolites, drugs and nutrients in a painless manner at controlled and consistent rates by means that avoid the digestive tract where the drugs or metabolites may be destroyed through the digestive process. It would be advantageous for these procedures and devices to perform automatically without patient intervention so that a controlled and constant level of therapeutic agent could be delivered to the patient.

SUMMARY OF THE INVENTION

The present invention provides a patch for the transdermal delivery of a therapeutic agent to a biological subject that includes a first electrode comprising a first array of electrically conductive microprojections for providing electrical communication through a skin portion of the subject to a second electrode comprising a second array of electrically conductive microprojections. The patch further includes a reservoir for holding the therapeutic agent surrounding the first electrode and a pulse generator for providing an exponential decay pulse between the first and second electrodes. An electronic control module may also be provided.

A second reservoir for holding a second therapeutic agent surrounding the second electrode may be provided. The therapeutic agent may be the same agent as is contained in the first reservoir or it may be a different agent. The one or more therapeutic agents are suspended in the reservoirs within a buffer gel. The buffer gel may be an agarose gel or may be selected from many iontophoretic gels that are commercially available. Selected buffer gels for the first and second reservoirs may be the same or the gels may be different.

The microprojections are adapted to provide perforation of the epidermis to a depth of between about 50 μm and about 150 μm. Preferably, the microprojections are adapted to transiently perforate the epidermis to a depth greater than the thickness of a stratum corneum layer of the epidermis but less than a depth of sensory nerve ending locations. This provides the desired passages cut through the stratum corneum but does not cut deeply enough to contact nerve endings, therefore resulting in painless delivery of the therapeutic agents. The diameters of the microprojections may range between about 0.5 μm and about 5 μm and the tips of the microprojections may have a diameter of between about 1 μm and about 2 μm The microprojections may be made of any of the materials known to those having ordinary skill in the art including, without limitation, tungsten, platinum, silicon, gold and silver. In some embodiments, the microprojections may be made of etched tungsten wire plated with platinum or gold or may be made of etched silicon block plated with platinum. Microprojections made with silicon are included in embodiments of the present invention and preferably, are plated with a metal, including platinum or gold.

In some embodiments of the present invention, the arrays may include between about 5 to 10 rows of microprojections by about 5 to 10 microprojections per row, or even between about 1 to 4 rows of microprojections by about 1 to 4 microprojections per row. However, the exact arrangement of the microprojections is not limiting.

The present invention may further include a conductive mount for securing the micro projections in an arranged layout of the array. The conductive mount may be made in many different forms and of different materials as known to those having ordinary skill in the art including, for example, a conductive mounting rod or a conductive mounting plate made of a silicon substrate plated with a conductive coating. The conductive mount may include a nonconductive substrate plated with a conductive coating. Examples of materials for the nonconductive substrate include polyvinylidene fluoride and polyethylene terephthalate. The conductive coating plated on the substrate may be, for example, a noble metal.

The present invention further includes an electrical power source, which may be selected from many available as known to those having ordinary skill in the art. Batteries are one suitable power source. Also included in the present invention is a power inverter for transforming DC current from the one or more batteries or other power source to AC current to the electrodes.

In one embodiment of the present invention, one or more therapeutic agents may be microencapsulated within a polymer matrix, such as within microspheres, which may be selected, for example, from a synthetic cationic copolymer, a synthetic anionic copolymer or formed from materials made of collagen or albumin.

The microspheres preferably have a diameter between about 5 microns and about 100 microns or more preferably between about 10 microns and about 70 microns. The therapeutic agent may be selectively microencapsulated within a polymer matrix that is negatively charged, positively charged, or has no charge, regardless of whether the therapeutic agent is negatively charged, positively charged, or has no charge.

In some embodiments of the present invention, the exponential decay pulse may be superimposed over a sign wave current. Alternatively, the exponential decay pulse may be superimposed over a constant current function to offset the constant current function to a net negative or a net positive current.

The present invention further provides methods for the transdermal delivery of a therapeutic agent that includes the steps of piercing a stratum corneum layer of skin with two arrays of conductive microprojections, encapsulating the therapeutic agent into biocompatible charged carriers, surrounding the conductive microprojections with the therapeutic agent, generating an exponential decay pulse between the two arrays of conductive microprojections to create a non-uniform electrical field and electrokinetically driving the therapeutic agent through the stratum corneum layer of skin.

In some embodiments of the present invention, the exponential decay pulse is generated using parameters comprising a number of pulses, a voltage range, and a time period. The number of pulses may range between about 100 and 300 per minute at a voltage range of between about 3 V and about 60 V. Preferably, the upper voltage range is between about 30 V and about 70 V and the lower voltage range may be between about 0.5 V and about 20 V. The time period for the exponential decay pulse may range, for example, between about 30 seconds and about 1 second in some embodiments and between about 10 seconds and about 2 seconds in others.

The foregoing and other objects, features and advantages of the invention will be apparent from the following more particular description of a preferred embodiment of the invention, as illustrated in the accompanying drawing wherein like reference numbers represent like parts of the invention.

DETAILED DESCRIPTION

The present invention provides methods and devices for the transdermal delivery of therapeutic agents to a biological subject. Therapeutic agents suitable for transdermal delivery include, for example, medications, prescription drugs, non-prescription drugs, nutrients and metabolites. The agents that are suitable for transdermal delivery may be positively charged, negatively charged or they may be neutral and have no charge at all. Furthermore, the therapeutic agents may optionally be encapsulated by neutral or charged polymeric materials to provide a particle having a desired charge that may be the same as or different than the charge on the therapeutic agent itself for transdermal delivery to a biological subject. Upon delivery into the biological subject, preferably the polymeric material degrades at a known rate, thereby releasing the therapeutic agent over a known period for a timed release of the agent.

To provide transdermal delivery of a wide range of therapeutic agents to a biological subject, a driving force is required that drives the therapeutic agents through the skin. The greatest barrier to the transdermal delivery of therapeutic agents is the stratum corneum, the top layer of the epidermis of the skin. To overcome this barrier to the transdermal delivery of therapeutic agents through the stratum corneum, the present invention provides sharp microprojections that cut micropassages through the stratum corneum. The present invention further utilizes electrokinetic transport techniques to drive the therapeutic agents along the microconduits and beyond the stratum corneum. Cutting micropassages through the stratum corneum reduces the electrical potential that must be applied across the skin when utilizing electrokinetic transport techniques.

In one preferred embodiment, a patch containing the therapeutic agent is applied to the skin. The patch includes two arrays of microprojections that cut the microconduits through the stratum corneum and also function as the electrodes that are required by the electrokinetic transport techniques. In their function as electrodes, the surface of the microprojections must be electrically conductive. For the surface to be electrically conductive, the microprojections may be fashioned from electrically conductive materials or, alternatively, may be fashioned of a non-electrically conductive substrate that is coated or plated with an electrically conductive material.

The microprojections of the present invention that are used to cut the stratum corneum do not penetrate the skin to the dermis layer, which is the layer of skin below the epidermis layer that contains the sensory nerve endings. Because the microprojections do not penetrate to the depth of the sensory nerve endings, the microprojections painlessly perforate the stratum corneum to provide microconduits in the skin through which the therapeutic agents may be driven by electrokinetic transport techniques.

The microprojections may be made from materials that have sufficient strength and manufacturability to produce blades, such as, glasses, ceramics, rigid polymers, metals and metal alloys. Examples of metals and metal alloys include, but are not limited to, stainless steel, iron, steel, tin, zinc, copper, platinum, aluminum, germanium, nickel, zirconium, titanium and titanium alloys consisting of nickel, molybdenum and chromium, metals plated with nickel, gold, rhodium, iridium, titanium, platinum, and the like. An example of glasses includes a devitrified glass such as "PHOTOCERAM" available from Corning in Corning, N.Y. Examples of polymers include, but are not limited to, rigid polymers such as polystyrene, polymethylmethacrylate, polypropylene, polyethylene, "BAKELITE", cellulose acetate, ethyl cellulose, styrene/acrylonitrile copolymers, styrene/butadiene copolymers, acrylonitrile/butadiene/styrene (ABS) copolymers, polyvinyl chloride and acrylic acid polymers including polyacrylates and polymethacrylates. However, as noted above, if a non-electrically conductive material is used to form the microprojections, the microprojection substrate must be plated or coated with an electrically conductive material.

While the microprojections may be made of many different types of materials, preferred materials include tungsten, platinum, silicon, gold and silver. One preferred embodiment includes microprojections made of etched tungsten wire that is plated with platinum. Another preferred embodiment includes microprojections that are made of etched silicon plated with platinum, gold, silver or other noble metals. Methods of manufacturing arrays of microprojections are well known to those having ordinary skill in the art.

The microprojections preferably have a diameter of between about 0.5 μm and about 5 μm at the tip. More preferably, the microprojections have a diameter of between about 1 μm and about 2 μm at the tip. In the proximal direction from the tip, the shafts of the microprojections are typically about 0.25 mm but may range between about 0.05 mm and about 0.5 mm.

Because the thickness of the human epidermis is between about 50 μm and about 150 μm, the length of the microprojections for human use preferably ranges between about 50 μm and about 250 μm, more preferably between about 150 μm and about 200 μm. However, since the device may be used on other animals as well, the microprojections are typically of sufficient length to penetrate the stratum corneum layer of the epidermis of a particular animal or group of animals, but preferably not so long as to penetrate into the dermis layer and make contact with the sensory nerve endings.

The present invention includes cutting a plurality of microconduits through the stratum corneum by using arrays of the microprojections. Because the microconduits that are cut through the stratum corneum significantly decrease the current and potential required by the electrokinetic transport techniques, increasing the number of microconduits that are cut through the stratum corneum decreases the current and potential requirements of the electrokinetic techniques.

The microprojections may have hooks on the tips. Hooks or barbs are often fashioned on the tips of the microprojections to anchor them to the skin and are often preferred in order for the microprojections to remain in a skin-piercing relationship with the skin at all times.

The microprojections are arranged on an electrically conductive mount or base that secures the microprojections in the preferred layout of the array. The conductive mount may be formed as, for example, a conductive mounting rod or a conductive mounting plate. If the microprojections are fashioned from a block of silicon, then the silicon block forms the substrate of the conductive mounting block. Like the microprojections, the conductive mount must be electrically conductive since the conductive mounts form part of the electrodes that are required by the electrokinetic transport techniques. Therefore, the conductive mounts may be formed of materials that are electrically conductive or the conductive mounts may be formed of a non-electrically conductive substrate coated or plated with a conductive material. In one preferred embodiment, the conductive mount is made of non-conductive materials selected from polyvinylidene fluoride or polyethylene terephthalate as a nonconductive substrate, which is then plated with a noble metal to make the mount conductive. The mount may be made from any of the materials disclosed earlier as being suitable for making the microprojections.

In one embodiment of the present invention, the electrokinetic transport techniques that are used to drive the therapeutic agents across the stratum corneum include electroosmosis, iontophoresis, dielectrophoresis or combinations thereof. Iontophoresis involves the electrically induced transport of charged ions. Typically, relatively low transdermal voltage of between about 0.1 V and about 5 V can be used to electrokinetically transport the therapeutic agents having either a negative or positive charge. Electroosmosis involves the movement of a solvent containing the therapeutic agent through a membrane under the influence of an electric field. Dielectrophoresis involves the polarization and associated motion induced in particles by a non-uniform electric field. The phenomenon arises from the difference in the magnitude of the force experienced by the electrical charges within an unbalanced dipole, induced when a non-uniform electric field is applied. In a non-uniform field, the convergence of the field lines encourages uneven charge alignment and formation of an induced dipole moment. More simply, dielectrophoresis is defined as the lateral motion imparted on uncharged particles as a result of polarization induced by non-uniform electric fields.

Therefore, non-uniform electrical fields must be generated to induce transdermal delivery of the therapeutic agents through the microchannels when using dielectrophoresis as the driving force. A preferred embodiment of the present invention provides an electronic control module that includes a pulse generator to generate an exponential decay pulse between the two arrays of microprojections that are part of the two electrodes. An exponential decay pulse is preferred due to the long duration of voltage changes on decay, thereby creating the non-uniform electric field required for dielectrophoresis. Parameters to be considered in generating the pulse include the starting and ending voltage of the pulse, the number of pulses over a set period of time and the pulse resolution. These parameters may be varied for different applications of transdermal transport of therapeutic agents.

In a preferred embodiment, the electrodes are powered by a power source that is one or more batteries although other suitable power sources are acceptable. Preferably, the batteries provide between about 5 V and 10 V and more preferably, between about 7 V and 8 V. Capacity of the batteries are typically between about 1500 mAh and about 3500 mAh, preferably between about 2300 mAh and about 2500 mAh. An example of a suitable battery power supply is two photo DL123 lithium batteries.

Figure 1A:
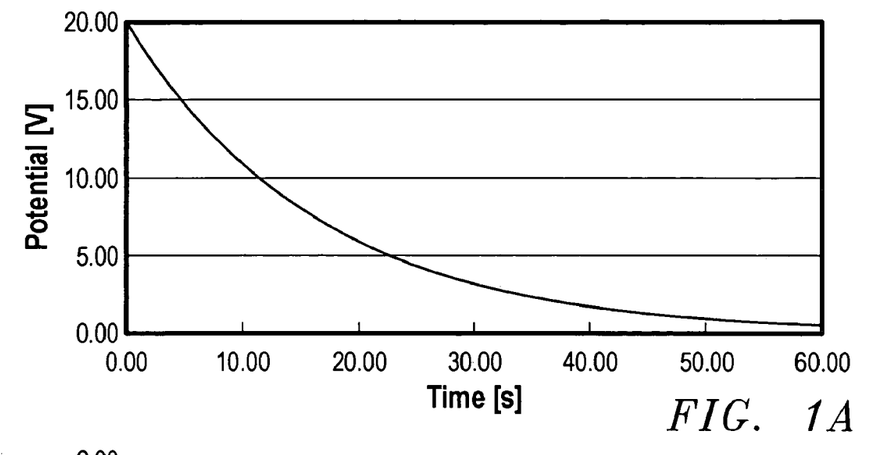
FIGS. 1A-C are graphs showing an exponential decay pulse, a sign function current, and the pulse obtained when the sign function current is superimposed on the decay pulse in accordance with the present invention.
Figure 1B:
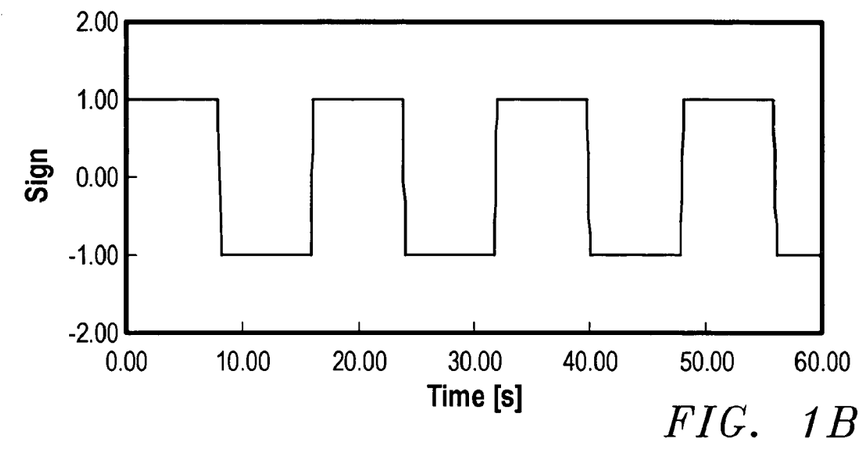
Figure 1C:
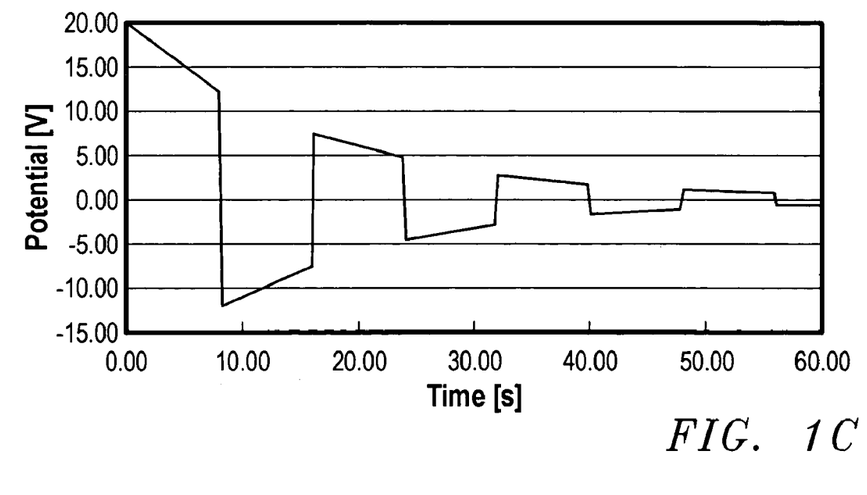

The DC current may be used in the present invention to provide the electrokinetic transport techniques to drive the therapeutic agent through the stratum corneum. However, a preferred device includes a power inverter to convert the DC current, or even an AC current, to a desired AC current. When the AC current is superimposed on the exponential decay type pulse, the greatest non-uniform electrical field is generated to create the highest level of dielectrophoresis as the transdermal delivery driving force. FIGS. 1A-C are graphs showing an exponential decay pulse, a sign function current, and the pulse obtained when the sign function current is superimposed on the decay pulse.

The electrokinetic transport of particles having a neutral charge occurs only by the slower technique of electroosmosis. Electrokinetic techniques are more efficient using iontophoresis and dielectrophoresis on charged particles. Particles having a positive charge are successfully delivered transdermally from the anode electrode because positively charged particles are attracted by the cathode electrode. Likewise, particles having a negative charge are successfully delivered transdermally from the cathode electrode because negatively charged particles are attracted by the anode electrode.

To maximize the transdermal delivery of therapeutic agents, the charge of the particle to be transdermally delivered may be controlled by encapsulating the therapeutic agent in a polymeric material having the desired charge. One advantage of such a method is that it facilitates the delivery of the therapeutic agent from both electrodes at once. For example, if the therapeutic agent naturally held a positive charge, the agent would have to be delivered only from the anode side of a device utilizing electrokinetic transport techniques. However, by encapsulating a portion of the therapeutic agent with a negatively charged polymeric material, the negatively charged microspheres can also deliver the therapeutic agent into the biological subject from the cathode side of the device, thereby increasing, perhaps even doubling, the amount of agent that can be delivered.

Methods for encapsulating therapeutic agents in polymeric material are well known to those having ordinary skill in the art. Polymeric materials may be used that encapsulate neutral, negatively charged, or positively charged therapeutic agents in microcapsules having a positive, negative or neutral charge As is known to those having ordinary skill in the art, the microcapsules degrade harmlessly within the biological subject into which they were delivered, thereby releasing the therapeutic agent contained within the microcapsules. In one preferred embodiment, the therapeutic agent is encapsulated in microspheres measuring approximately 10 μm. Examples of suitable polymers that may be used for microencapsulation are shown in Table 1. EUDRAGIT is a registered trademark of Rohm&Hass, a German company.

TABLE 1

Example Polymers for Encapsulation

| Polymer | Source | Crosslinking Agent | Degradation Mechanism |
| --- | --- | --- | --- |
| Collagen | Cartilage | glutaraldehyde | NA |
| Albumin | Serum | glutaraldehyde | NA |
| poly(Lactic acid) | Synthetic | none | base hydrolysis |
| poly(Lactide-co-glycolide) | Synthetic | none | base hydrolysis |
| poly(Hydroxy butyrate) | Alcaligenes bacteria | none | enzymatic hydrolysis |
| EUDRAGIT E100 (cationic copolymer) | Synthetic | none | hydrolysis |
| EUDRAGIT L100 (anionic copolymer) | Synthetic | none | hydrolysis |

In a preferred embodiment, the microspheres are suspended in a buffer gel, such as an agarose gel. The gel is held within a reservoir that surrounds the array of microprojections. Therefore, when the microprojections cut through the stratum corneum, the microspheres that are suspended in the gel can flow through the gel under the electrokinetic driving force, through the microconduits cut by the microprojections and into the biological subject.

Figure 2:
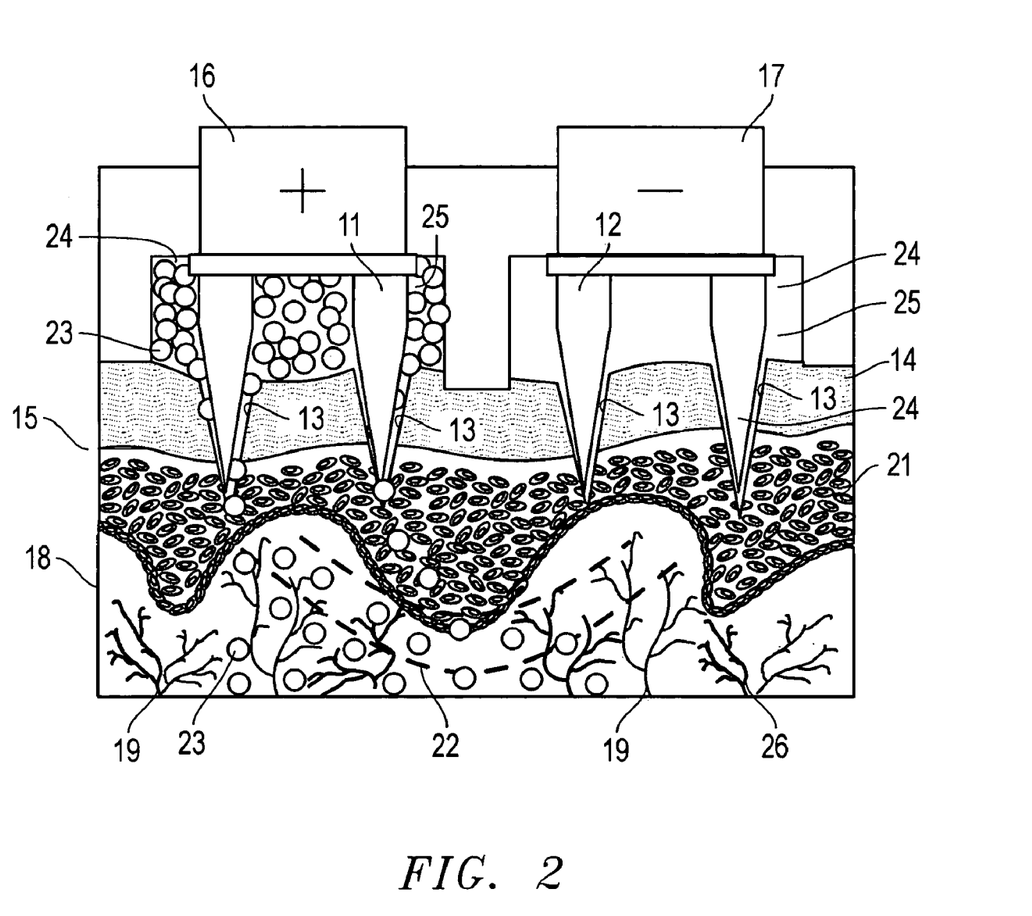
FIG. 2 is a cross sectional view of microprojections inserted through the stratum corneum with microspheres containing a therapeutic agent being driven through the microconduits by electrokinetic transport forces in accordance with the present invention.

FIG. 2 is a cross sectional view of microprojections inserted through the stratum corneum with microspheres containing a therapeutic agent being driven through the microconduits by electrokinetic transport forces in accordance with the present invention. Two arrays of microprojections 11, 12 are used to cut microconduits 13 through the stratum corneum 14 layer of the epidermis 15. Each of the microprojections in the arrays 11, 12 are held in place by a conductive mount 16, 17, respectively. It should be noted that the microprojections on the arrays 11, 12 do not extend to the dermis layer 18 of the skin that contains sensory nerve endings so there is no pain associated with piercing the stratum corneum 14 with the microprojections of the arrays 11, 12. The microprojections of the arrays 11, 12 extend only into the lower layer of the epidermis 15, which is the stratum malphigii 21.

Both the conductive mounts 16, 17 and the microprojections in the arrays 11, 12 are electrically conductive, either because the parts are formed entirely of electrically conductive material or because they are coated or plated with an electrically conductive material such as a noble metal. A power source, not shown, is connected to the conductive mounts 16, 17 and a circuit is completed between the two arrays 11, 12 through the epidermal 15 and dermal 18 layers of the skin. Electric field lines 22 are formed through the skin layers 15, 18 to drive the positively charged microspheres 23 from the array 11 acting as the anode electrode to the array 12 acting as the cathode electrode.

Each of the arrays 11, 12 of microprojections are contained within reservoirs 24 containing a buffer gel 25. The buffer gel 25 surrounds the microprojections of the arrays 11, 12. As the electrical current is applied through the two arrays 11, 12, the microspheres 23 move through the gel to the microconduits 13 and into the skin layers 15, 18 where the therapeutic agent contained within the microspheres 23 will be absorbed by the blood capillaries 26.

Figure 3A:
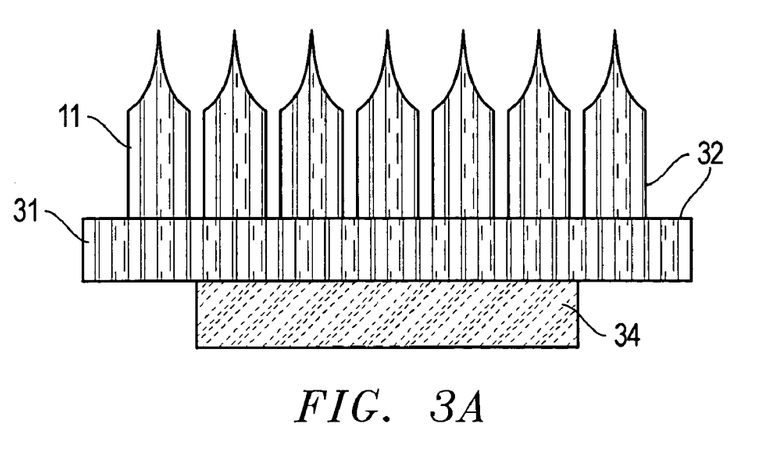
FIGS. 3A-B are a cross sectional view and a perspective view of an array of microprojections.
Figure 3B:
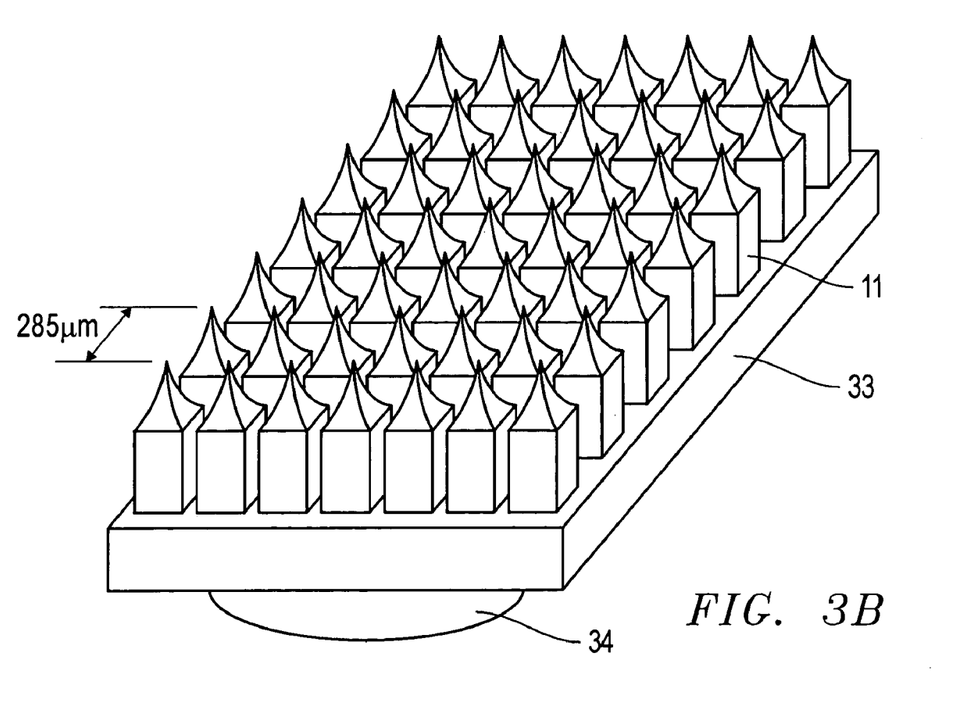

FIGS. 3A-B are a cross sectional view and a perspective view of an array of silicon microprojections. Each of the silicon microprojections 11 are about 200 μm in length and the silicon substrate 31 of the microprojections 11 is coated with a conductive coating 32, typically a noble metal, such as palladium, platinum, gold or silver. For example, plating platinum on the silicon substrate 31 may be accomplished using 2000A platinum sputter coated on a 200A chromium stick layer as known to those having ordinary skill in the art.

The microprojections 11 are etched from a block of silicon 33 before the base 33 and microprojections 11 are plated with the conductive coating 15. The array of microprojections 11 is then mounted on a conductive mounting rod 34 that is in electrical communication with the power source, not shown.

Figure 4:
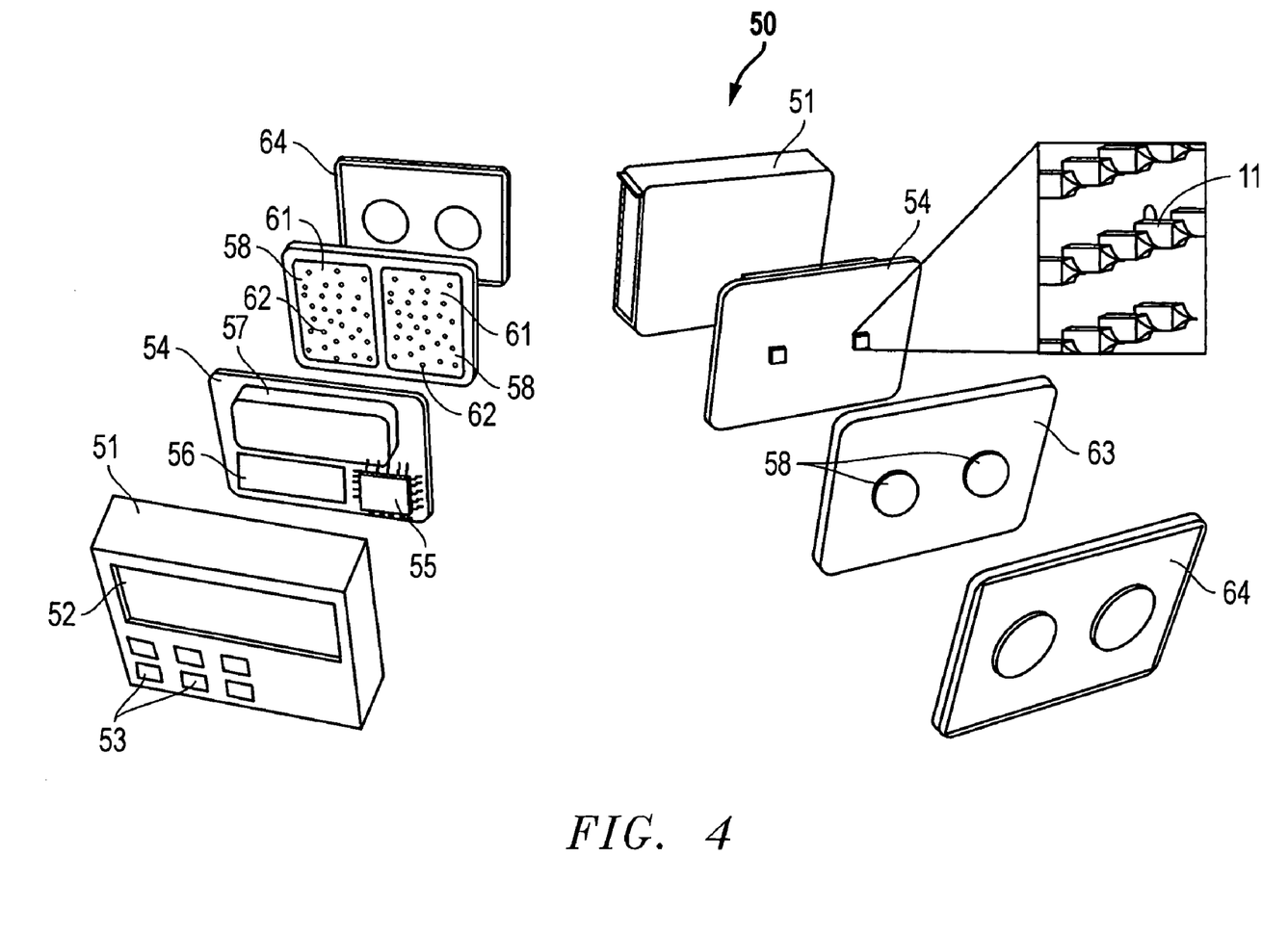
FIG. 4 is an exploded view of an exemplary device for the transdermal delivery of therapeutic agent in accordance with the present invention.

FIG. 4 is an exploded view of an exemplary device for the transdermal delivery of a therapeutic agent in accordance with the present invention, showing both front and back views. The therapeutic agent delivery device 50 includes a housing 51 having a display 52 for displaying information to the user and buttons 53 for querying the device 50 and for inputting information.

The electronics board 54 provides the electronic controls module required to monitor and control the device 50. The electronics control module includes an electronic computer chip 55 that provides the control functions as well as data and information storage. A battery 56 provides the power source and other electronics 57 are included on the electronics board such as a power inverter and pulse generator, neither shown. Also mounted on and protruding through the electronics board 54 are the arrays of microprojections 11.

The reservoirs 58 contain the gel 61 in which the therapeutic agent 62 is suspended. The therapeutic agent is typically encapsulated in a polymeric material. The microprojections 11 protruding through the electronics board 54 extend through the floor 63 of the reservoirs 58. The floor 63 of the reservoirs 58 may be coated with an adhesive to hold the device 50 on the user. When placed on a user, the microprojections 11 extending through the floor 63 of the reservoirs 58 cut microconduits through the stratum corneum of the user. A disposable protective cover 64 protects the microprojections 11 from damage until the device 50 is ready for use.

EXAMPLE 1

Microprojections were prepared using the following method. A small glass vial, having a diameter of about 2.5 cm, was filled with a solution used for electroetching wire into the microprojections. The vial was then closed with a plastic cap containing a septum. The solution used for electroetching depends upon the type of wire used for making the microprojections. For tungsten microprojections, the solution used was 0.1 M NaOH. For platinum microprojections, the solution used was saturated NaNO2 solution. For gold microprojections, the solution used contained 10 g KCN and 5 g KOH per 40 mL of water.

Three stainless steel needles were inserted through the septum so that the ends were about 5 mm above the solution level in the vial. A length of wire about 5 cm in length and having a thickness of about 0.25 mm, was inserted into the solution through the first needle to a depth of about 2 mm.

A second wire was inserted through the second needle and immersed in the solution shaped in a manner to form a spiral around the wire to be electroetched. When electroetching wire made of platinum or tungsten, the wire that was used to form a spiral around the wire to be electroetched was platinum, having a thickness of about 0.5 mm. When electroetching wire made of gold, the wire that was used to form a spiral around the wire to be electroetched was also gold, having a thickness of about 0.5 mm. The third stainless steel needle was used to vent the gas produced during the electroetching.

AC potentials of 10 V, 17 V, and 20 V were applied for the W, Pt and Au microprojections respectively. AC current was monitored during the electroetching. The microprojections were ready when the AC current dropped to zero. The microprojections that were formed had very sharp tips having diameters of between about 1 and about 2 micrometers.

EXAMPLE 2

A sample of pig's skin taken from a pig's foot was placed on a test cell sandwiched between the lower compartment and the top of the cell. The lower compartment of the cell was filled with 0.1 M phosphate buffer. A set of two arrays of conductive gold microprojections, each array having seven microprojections, was slowly moved towards the skin sample while measuring the resistance between the arrays. When the measured resistance dropped sharply from an open circuit reading to about 800 MΩ, the microprojections were known to be in contact with the skin sample and the reading on the micrometer was recorded as the "zero" location from which a precise penetration depth could be measured.

The arrays of microprojections were then raised above the skin sample and a suspension of microspheres in phosphate buffer was transferred into two compartments of the top portion of the cell. Typically, a 0.1 mL of suspension containing 10 mg of microspheres was used in each compartment. The microprojections were then inserted into the skin sample to the desired depth of penetration from the "zero" location determined above. Exponential decay pulses were applied to the arrays. For some of the experiments, the microprojections were removed from the skin after skin perforation and then the skin sample was subjected to pulses.

Parameters were varied during the experiments. The number of pulses varied from between 0 and 400; pulse duration varied from between 0 and 20 seconds; pulse amplitude varied from between 3 and 80 V; and skin sample penetration varied from between 100 μm and 250 μm.

After each experiment, the skin was removed from the cell, washed with DI water, and either placed in a vial containing 10% neutral-buffered formalin or frozen on dry ice. When ready for processing, the skin sample was washed, dehydrated using alcohol solutions up to 100% alcohol and embedded into paraffin. The skin was then sliced into thin sections for microscopic examination. Microscopic examination revealed the passage of the therapeutic agent into the skin at depths greater than the depth of penetration by the microprojections.

It will be understood from the foregoing description that various modifications and changes may be made in the preferred embodiment of the present invention without departing from its true spirit. It is intended that this description is for purposes of illustration only and should not be construed in a limiting sense. The scope of this invention should be limited only by the language of the following claims.

What is claimed is:

1. A device for transdermal delivery of a therapeutic agent to a biological subject, comprising:
   a first electrode comprising a first array of electrically conductive microprojections for providing electrical communication through a skin portion of the subject to a second electrode comprising a second array of electrically conductive microprojections;
   a reservoir for holding the therapeutic agent surrounding the first electrode;
   a pulse generator for providing an exponential decay pulse between the first and second electrodes; and
   an electronic control module.

2. The device of claim 1, further comprising a second reservoir for holding a second therapeutic agent surrounding the second electrode.

3. The device of claim 2, wherein the second therapeutic agent is the same therapeutic agent surrounding the first electrode.

4. The device of claim 2, further comprising a buffer gel contained in the reservoirs for suspending the therapeutic agents.

5. The device of claim 4, wherein the buffer gel is an agarose gel.

6. The device of claim 4, wherein the buffer gel is selected from iontophoretic gels.

7. The device of claim 2, wherein the buffer gel in the first reservoir is the same material as the buffer gel in the second reservoir.

8. The device of claim 1, wherein the microprojections are adapted to provide perforation of the epidermis to a depth of between about 50 μm and about 150 μm.

9. The device of claim 1, wherein the microprojections are adapted to transiently perforate the epidermis to a depth greater than the thickness of a stratum corneum layer of the epidermis but less than a depth of sensory nerve ending locations.

10. The device of claim 1, wherein the tip of the microprojections have a diameter of between about 0.5 μm and about 5 μm.

11. The device of claim 1, wherein the tip of the microprojections have a diameter of between about 1 μm and about 2 μm.

12. The device of claim 1, wherein the microprojections are made of materials selected from tungsten, platinum, silicon, gold or silver.

13. The device of claim 1, wherein the microprojections are made of etched tungsten wire plated with platinum or gold.

14. The device of claim 1, wherein the microprojections are made of etched silicon block plated with platinum.

15. The device of claim 1, wherein the microprojections are made of silicon.

16. The device of claim 15, wherein the microprojections are plated with platinum or gold.

17. The device of claim 15, wherein the microprojections are plated with a metal.

18. The device of claim 1, wherein each of the arrays measure between about 5 to 10 microprojections by about 5 to 10 microprojections.

19. The device of claim 1, wherein each of the arrays measure between about 1 to 4 microprojections by about 1 to 4 microprojections.

20. The device of claim 1, wherein each of the electrodes further comprise a conductive mount for securing the micro projections in an arranged layout of the array.

21. The device of claim 20, wherein the conductive mount is a conductive mounting rod.

22. The device of claim 20, wherein the conductive mount is a conductive mounting plate.

23. The device of claim 20, wherein the conductive mount comprises a silicon substrate plated with a conductive coating.

24. The device of claim 20, wherein the conductive mount comprises a nonconductive substrate plated with a conductive coating.

25. The device of claim 24, wherein the nonconductive substrate is selected from polyvinylidene fluoride or polyethylene terephthalate.

26. The device of claim 24, wherein the conductive coating is a noble metal.

27. The device of claim 1, further comprising a power source.

28. The device of claim 27, wherein the power source is one or more batteries.

29. The device of claim 28, further comprising a power inverter for transforming DC current from the one or more batteries to AC current to the electrodes.

30. The device of claim 1, wherein the therapeutic agents are microencapsulated within a polymer matrix.

31. The device of claim 30, wherein the polymer matrix is a synthetic cationic copolymer.

32. The device of claim 30, wherein the polymer matrix is a synthetic anionic copolymer.

33. The device of claim 30, wherein the polymer matrix is formed of materials selected from collagen or albumin.

34. The device of claim 30, wherein the therapeutic agents are microencapsulated within micro spheres.

35. The device of claim 34, wherein the microspheres are between about 5 microns and about 100 microns.

36. The device of claim 34, wherein the microspheres have a diameter of between about 10 microns and about 70 microns.

37. The device of claim 30, wherein the therapeutic agent is negatively charged, the therapeutic agent is selectively microencapsulated within a polymer matrix that is negatively charged, positively charged, or has no charge.

38. The device of claim 30, wherein the therapeutic agent is positively charged, the therapeutic agent is selectively microencapsulated within a polymer matrix that is negatively charged, positively charged, or has no charge.

39. The device of claim 30, wherein the therapeutic agent has no charge, the therapeutic agent is selectively microencapsulated within a polymer matrix that is negatively charged, positively charged, or has no charge.

40. The device of claim 1, wherein the exponential decay pulse is superimposed over a sign wave current.

41. The device of claim 1, wherein the exponential decay pulse is superimposed over a constant current function to offset the constant current function to a net negative or a net positive current.

42. A method for transdermal delivery of a therapeutic agent, comprising:
   piercing a stratum corneum layer of skin with two arrays of conductive microprojections;
   encapsulating the therapeutic agent into biocompatible charged carriers;
   disposing the conductive microprojections into contact with the therapeutic agent;
   generating an exponential decay pulse between the two arrays of conductive microprojections to create a non-uniform electrical field; and
   electrokinetically driving the therapeutic agent through the stratum corneum layer of skin.

43. The method of claim 42, wherein the exponential decay pulse is generated using parameters comprising a number of pulses, a voltage range, and a time period.

44. The method of claim 43, wherein the number of pulses are between about 100 and 300 per minute.

45. The method of claim 43, wherein the voltage range is between about 60 V and about 3 V.

46. The method of claim 43, wherein the upper voltage of the voltage range is between about 70 V and about 30 V.

47. The method of claim 43, wherein the lower voltage of the voltage range is between about 20 V and about 0.5 V.

48. The method of claim 43, wherein the time period is between about 30 seconds and about 1 second.

49. The method of claim 43, wherein the time period is between about 10 seconds and about 2 seconds.

* * * * *